United States Patent [19]

Boron

[11] Patent Number: 4,699,014
[45] Date of Patent: Oct. 13, 1987

[54] MOLTEN METAL SAMPLER WITH SAND CAST MOLD PART

[75] Inventor: Joseph J. Boron, Medina, Ohio

[73] Assignee: Midwest Instrument Co., Inc., Hartland, Wis.

[21] Appl. No.: 886,139

[22] Filed: Jul. 24, 1986

[51] Int. Cl.[4] .............................................. G01N 1/12
[52] U.S. Cl. .............................. 73/864.57; 73/864.55; 73/864.58; 374/140
[58] Field of Search ........... 73/864.57, 864.56, 864.55, 73/864.53, 864.59, 864.58, 864.54, DIG. 9; 374/26, 139, 140; 249/DIG. 4

[56] References Cited

U.S. PATENT DOCUMENTS

| | | | |
|---|---|---|---|
| 3,481,201 | 12/1969 | Falk | 374/140 X |
| 3,646,816 | 3/1972 | Hance et al. | 73/864.56 |
| 3,774,453 | 11/1973 | Falk | 73/864.56 X |
| 3,913,404 | 10/1975 | Boron | 73/864.56 |
| 3,983,755 | 10/1976 | Collins | 73/864.56 X |
| 4,140,019 | 2/1979 | Falk | 73/DIG. 9 |
| 4,326,426 | 4/1982 | Falk | 73/864.59 |
| 4,503,716 | 3/1985 | Wuensch | 73/864.57 |
| 4,521,639 | 6/1985 | Falk | 374/139 X |
| 4,565,101 | 1/1986 | Boron | 73/864.57 |

FOREIGN PATENT DOCUMENTS 2845566  4/1979  Fed. Rep. of Germany ... 73/864.57

Primary Examiner—Tom Noland
Attorney, Agent, or Firm—Fuller, Puerner & Hohenfeldt

[57] ABSTRACT

Disclosed herein is a molten metal sampler made from cast mold halves which are preassembled in a paperboard sleeve which is filled with sand-resin mix, which is then baked. The sampler is provided with windows on one sample cavity which are provided with metal plates which form the sides for sample mold and provide smooth sides for the sample. Various thickness plates can be employed to fit within the windows. The sampler is also provided with a bath thermocouple and a liquidus arrest thermocouple. The sample formed has a thick disc portion suitable for spectrographic analysis and a wafer portion suitable for punching for gas analysis.

8 Claims, 5 Drawing Figures

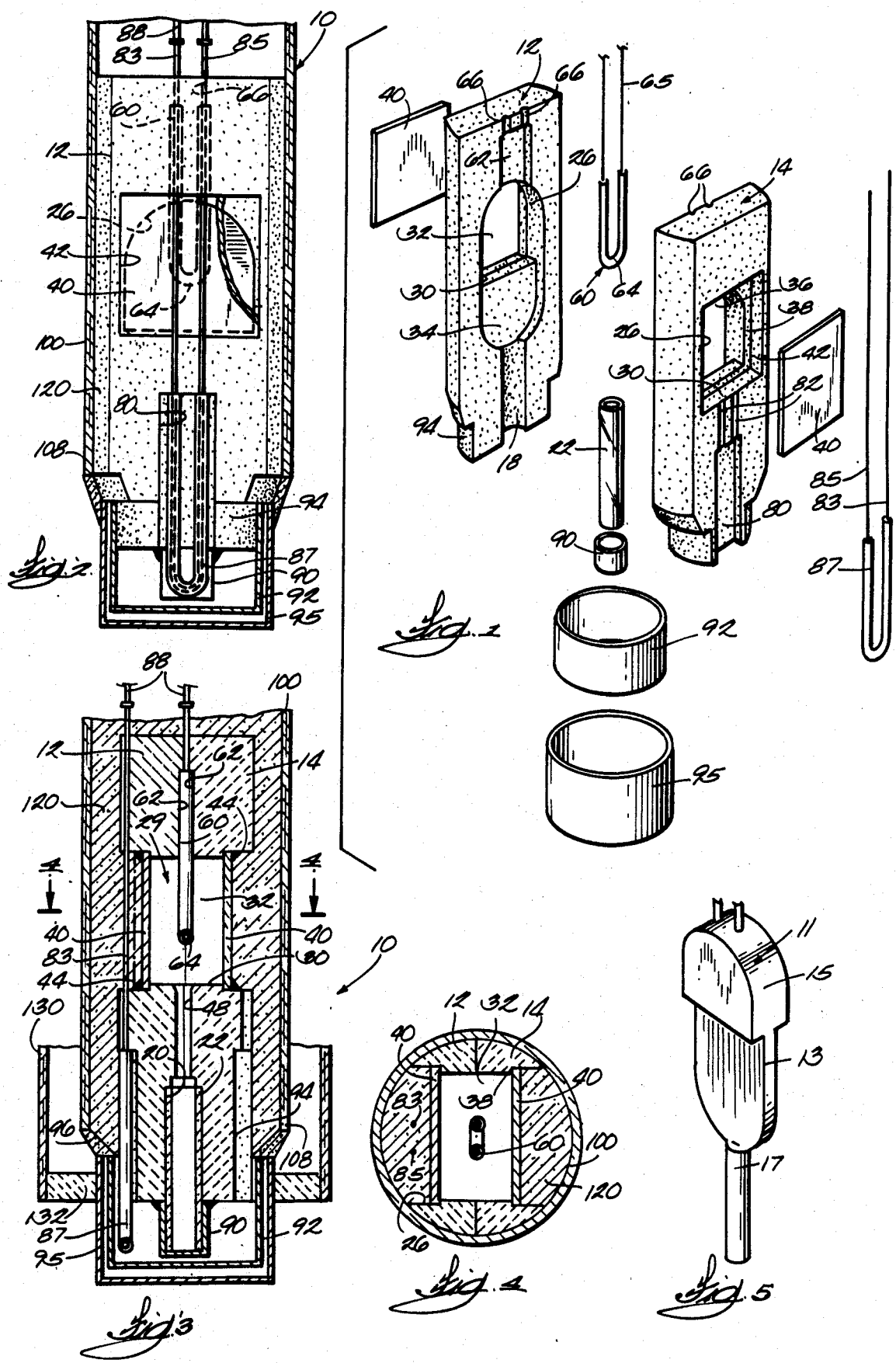

MOLTEN METAL SAMPLER WITH SAND CAST MOLD PART

FIELD OF THE INVENTION

The invention relates to a molten metal samplers provided with an internal thermocouple located in a chamber for liquidus carbon determination.

BACKGROUND OF INVENTION

The sampler of the invention is formed from opposed mold parts and is a further development of the subject matter disclosed in my U.S. Pat. No. 4,565,101 issued Jan. 21, 1986. That patent shows opposed mold halves formed from thermosetting foundry sand with recesses which cooperate to provide molten metal flow passages and the sample mold cavities. The sampler in that patent is intended to provide pin or rod-like samples. The present invention is involved with providing both a pin and paddle shaped sample with a wafer thin sample zone which is suitable for punching of pellets for combustion analysis.

In the present invention, the mold halves are encased in a cardboard tube which holds the mold parts in assembly. The gaps between the cardboard sleeve and the sample mold parts are filled with a thermosetting sand mix which is baked to hold the parts together. Prior art patents such as U.S. Pat. Nos. 4,326,426 issued Apr. 27, 1982 and 4,521,639 issued June 4, 1985, show the use of loose sand fill but not a baked sand fill. The baked sand mix of the present invention holds the parts, such as thermocouple wires, in positive position as hereinafter described. Other prior art relating to the subject matter of the invention includes U.S. Pat. No. 4,503,716 issued Mar. 12, 1985, which shows a sample with a thin wafer portion which can be punched to recover pellets for analysis. U.S. Pat. No. 4,140,019 discloses the use of thin metal chill plates to form the sides of a sample and cavity and provide a smooth surface on the sample sides as well as chill the metal. German Offenlegungsschrift No. 28 45 566 also shows a sample with a wafer portion extending from a thicker portion which is suitable for punching.

SUMMARY OF THE INVENTION

The invention provides a versatile molten metal sampler which incorporates a bath temperature thermocouple and a cooling curve thermocouple in a liquidus arrest chamber sample cavity. Ease in manufacture and saving of costs is afforded by the use of identical mold halves formed from molded thermosetting sand mix baked in an oven. Gas setting sand could also be employed. The mold halves are provided with appropriate recesses which cooperate to provide a fill passage and a sample mold with a thick portion and a thin wafer portion. Refractory cement coating on some sand parts provides a smooth finish for the sample. Wall means defining recesses form windows adjacent part of the sample mold cavity to receive chill plates which seal the windows and provide a chill on the sample and also provide a smooth surface on the sample disc portion opposite the metal plates. The type of metal involved for the chill plates and the thickness of the chill plates can be selected for appropriate bath conditions as hereinafter described. The thermocouple wires for the bath thermocouple are arranged along the side of the samplers and extend past the metal plates which cover the windows. The mold parts are held in assembly and the thermocouple wires positively positioned by assembling the mold halves in a paper sleeve which is then filled with a thermosetting sand resin mix which is baked or otherwise hardened to rigidify the assembly. Any suitable foundry sand-resin mix is appropriate. Gas setting mixes can be employed.

In prior art sensors which provide an internal chamber for the liquidus carbon determination the sample so obtained can be contaminated by the combustion residue from the cardboard exterior of the sensor lance. FIG. 11 of U.S. Pat. No. 3,481,201 is an example of this type of sampler. Moreover, the cylindrical sample obtained with such a lance must be cut to expose a flat surface for spectrographic analysis. The sample formed in that patent is also prone to internal voids. In prior art liquidus measuring devices with an end fill passage the molten metal commonly solidifies prematurely and an accurate liquidus arrest temperature is not obtained. With the present invention, the sample metal is directed through a thin passage prior to entry into the liquidus chamber. During a vertical immersion, the thin portion of the sample solidifies rapidly thus preventing molten metal in the thick portion from running out of the sample mold. The liquidus carbon reading is recorded as the sensor lance is withdrawn. The thick flat portion of the sample obtained from the liquidus chamber can be polished for spectrographic and x-ray analysis. The thin portion can be punched for a combustion type analysis.

Various of the features of the invention will become apparent from the disclosure.

DESCRIPTION OF DRAWINGS

FIG. 1 is an exploded perspective view of the sampler parts of the invention;

FIG. 2 is an enlarged side elevational view of the part shown in FIG. 1;

FIG. 3 is an enlarged end view of the assembled parts shown in FIGS. 1 and 2;

FIG. 4 is a sectional view along line 4—4 of FIG. 3; and

FIG. 5 is a perspective view of the sample formed from the sampler of the invention.

DESCRIPTION OF PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

A sampler 10 is formed from opposed mold parts 12 and 14 which are identical in shape and formed from the same mold. They are desirably formed from a thermosetting resin and sand and baked in the mold. A sample 11 (FIG. 5) is formed from the sampler cavities of the sampler 10 and has a wafer portion 13 for punching pellets and a thick portion 15 for spectrographic analysis. A pin 17 is also formed by the fill tube.

The mold halves 12 and 14 are provided with various recesses which cooperate to provide passages. Mold halves 12 and 14 are each provided with a recess 18 which cooperate to form a passage 20 which receives and embraces a fill tube 22 which can be constructed of fused quartz.

Each mold half 12 and 14 is provided with wall means 26 which define a oval sample compartment 29. The sample compartment is divided by a transverse sill 30 into an upper liquidus arrest chamber 32 which forms sample portion 15 and a lower wafer sample portion 34 for forming the wafer 13. The sill 30 forms the base for a through window 36 which is square in configuration. The dimensions of the window are slightly larger than the width of the liquidus arrest chamber 32 and hence a shoulder 38 surrounding the window provides a seat for chill plates 40. The wall means 42 defining the window has sufficient depth to accommodate various thickness plates 40 or one or more plates which are cemented in place with a refractory cement 44 during assembly. Some steel mills need more or less chill depending on whether they run their furnaces at relatively hot or cool temperatures. The appropriate chill plate also is selected to provide the desired cooling curve for determining the liquidus arrest temperature. The metal plates form the sides for the liquidus arrest chamber and the curved walls of the sampler form the end walls. The chill plates together with the sill and the wall means 26 provide a sample mold chamber of sufficient size to allow adequate super heat in the sampler for accurate carbon analysis for high carbon, low temperature heats. The liquidus chamber 32 is open adjacent the sill. The sill does not span the thickness of the walls defining the window and hence a thin passage 48, FIG. 3, between the fill tube and the chamber 32 provides a molten metal flow passage into the liquidus arrest chamber 32. The thin flow passage insures that the initial incoming metal from the metal that may be contaminated with residue from the protective caps (hereinafter described) and slag is swept completely through the wafer portion 13 into the upper liquidus chamber 32 to provide for a pure wafer sample 13.

Some prior art carbon-thermocouple lances with an end fill do not provide for adequate retention of sample metal in the liquidus arrest chamber as the sample is withdrawn. In the present invention, the thin passage 48 which forms the wafer portion 13 of the sample restricts outflow of the metal as the lance is removed from the bath. Also, the thin metal ribbon in the thin passage 48 cools rapidly. Hence, complete filling of the reservoir or chamber 32 without loss of metal is more consistent to provide for more accurate and consistently repeatable cooling curves.

A fused quartz thermocouple U-tube 60 for measuring the cooling curve is positioned in the recess 62 and has a tip 64 approximately centered in the reservoir 32. The thermocouple wires 65 are guided by recesses 66 and extend upwardly for remote connection to lead wires. The mold halves 12 and 14 are also provided with exterior recesses 80 and 82 for the thermocouple wires 83 and 85 which fit therein. Shown in FIG. 2, the bath temperature thermocouple U-tube 87 nests in the recess 80. The tube 87 can be preassembled in recess 80 with refractory cement in that location. The thermocouple wires 83 and 85 will extend past the window 40 for connection to lead wires 88 at a point remote from the hot sample metal. This provides a cold junction at an isolated point to eliminate the generation of an secondary EMF which could give false readings. If the cold junction were located adjacent the window 40, high temperatures in that area could result in providing a false reading and distort the liquidus arrest measurement.

Various protective devices are enclosed at the inlet end. A fusible cap 90 is cemented to the fused quartz fill tube 22. A paperboard cap 92 fits over a necked down end 94 on the sample mold to provide a concentric annular surface. An outer thin metal fusible cap 95 covers the entire tip assembly. These parts can be cemented in place by refractory cement at 96 to seal the two outer caps relative to the mold.

Finishing of the sample mold includes use of an outer paperboard sleeve 100 which tightly receives the walls of the mold parts 12 and 14 and holds them tight assembly. The cardboard sleeve terminates at 108 as shown in FIG. 3 and refractory cement 96 fills the gap. The interior sleeve 100 and the gaps and cracks around the sample mold parts are positively positioned and sealed by a fill of a sand resin mix 120 which is introduced into the paperboard sleeve which is baked or otherwise hardened in place. This holds the mold parts 12 and 14 together and holds the thermocouple wires 83 and 85 in positive position. This insures stability of the thermocouple connection. The assembly of parts thus described ultimately may be encapsulated in a larger diameter paperboard tube or lance 130 and sealed at the end with refractory cement 132 as is conventional in the art.

I claim:

1. A molten metal sampler including wall means defining mold halves to form a sample mold with a thick disc sample portion and a contiguous thin portion, each of said mold halves having corresponding recesses which together form a sample mold cavity and recesses for an inlet passage, wall means defining window openings with shoulders at the sides of the thick disc mold portions and wall means defining recesses adjacent said shoulders to receive and support metal chill plates abutting said shoulders, aaid shoulders maintaining said chill plates in parallel spaced relationship and preventing said plates from falling into said mold cavity, said chill plates being larger than the window defined by said shoulders defining the side walls for the thick disc portion of the mold cavity and wall means defining opposed ledges in said mold halves, said opposed ledges forming the side walls for a thin wafer sample portion extending continuously from the mold portion forming said thick disc sample portion.

2. The molten metal sampler of claim 1 wherein the recesses defining the inlet or fill passage communicate with the recesses which form the thin wafer portion to afford filling of the sample mold by molten metal flow through the thin sample flow passage into the thick sample mold portion.

3. The sample mold in accordance with claim 1 wherein the ledges are coated with refractory cement to provide smooth surfaces on the sample.

4. A sampler in accordance with claim 1 wherein wall portions defining the sample mold end walls are coated with refractory cement.

5. A sampler in accordance with claim 1 wherein said mold halves have exterior longitudinal recesses to receive a thermocouple tube and support it therein.

6. A sampler in accordance with claim 5 including a thermocouple tube cemented in said recess and thermocouple wires extending past said window for remote connection to lead wires.

7. A sample in accordance with claim 6 wherein said sample mold parts and thermocouple wires are enclosed in a paperboard sleeve filled with a baked sand-resin mix.

8. A sampler in accordance with claim 1 wherein said mold halves have opposed internal recesses which cooperate to provide a channel for supporting a thermocouple tube for measuring liquidus arrest temperature.

* * * * *